United States Patent [19]

Ten Haken et al.

[11] 4,404,213

[45] Sep. 13, 1983

[54] DERIVATIVES OF CERTAIN PYRIDYLIMINOMETHYL-BENZENES

[75] Inventors: Pieter Ten Haken, Eastling, Nr Faversham; Shirley B. Webb, Sheldwich, Nr Faversham, both of England

[73] Assignee: Shell Oil Company, Houston, Tex.

[21] Appl. No.: 367,210

[22] Filed: Apr. 12, 1982

Related U.S. Application Data

[60] Division of Ser. No. 228,427, Jan. 26, 1981, Pat. No. 4,355,035, which is a continuation of Ser. No. 130,681, Mar. 17, 1980, abandoned.

[51] Int. Cl.$^3$ .................... A01N 43/40; C07D 213/74
[52] U.S. Cl. ..................................... 424/263; 546/305
[58] Field of Search .......................... 546/305; 424/263

[56] References Cited

U.S. PATENT DOCUMENTS

| | | | |
|---|---|---|---|
| 2,472,292 | 6/1949 | Friedman et al. | 542/424 |
| 2,513,996 | 7/1950 | Haury | 546/304 |
| 3,472,743 | 10/1969 | Rushmere | 204/554 |
| 3,832,351 | 8/1974 | Tanaka et al. | 546/305 |

FOREIGN PATENT DOCUMENTS

| | | |
|---|---|---|
| 816 | 2/1979 | European Pat. Off. . |
| 15628 | 9/1980 | European Pat. Off. . |
| 50-94133 | 7/1975 | Japan . |

OTHER PUBLICATIONS

R. D. Rich, "The Rates of Reaction of Aminopyridines with Benzaldehyde and of Pyridinecarboxaldehydes with Aniline," 1968, University Microfilms, Ann Arbor, Mich.

Baiocchi et al., Ann. Chim., (Rome), 1968, vol. 58 (6), pp. 608–614.

*Primary Examiner*—Henry R. Jiles
*Assistant Examiner*—Natalia Harkaway

[57] ABSTRACT

Derivatives of certain pyridyliminomethylbenzenes, useful as fungicides.

7 Claims, No Drawings

DERIVATIVES OF CERTAIN PYRIDYLIMINOMETHYL-BENZENES

This is a division of application Ser. No. 228,427, filed Jan. 26, 1981, which was a continuation of application Ser. No. 130,681, filed Mar. 17, 1980, abandoned. Application Ser. No. 228,427 has issued as U.S. Pat. No. 4,355,035.

DESCRIPTION OF THE INVENTION

This invention relates to certain derivatives of pyridyliminomethylbenzenes, these derivatives being described by the formula:

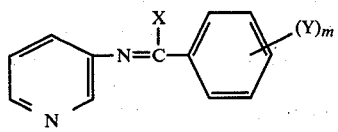

wherein X is alkoxy, haloalkoxy, alkylthio of from one to six carbon atoms; m is 1 or 2; and Y is halogen.

The pyridyliminomethylbenzenes of Formula I form acid-addition salts, for example, salts of hydrohalic acids, particularly of hydrochloric acid, or of sulfuric acid. Such salts are also of interest as having the fungicidal activity of the pyridyliminomethylbenzenes from which they are formed (in a manner well known per se), and, accordingly, are included within the scope of the present invention. It is also noted that the salt should be non-phytotoxic (which can readily be determined by routine test), since normally this is a requirement of fungicidal compositions.

Preferred halogen substituents are chlorine, fluorine and bromine atoms, chlorine being particularly preferred.

Preferred compounds of the invention are those wherein m is one and the substituent Y is attached at the 4-position of the benzene ring. Preferably, $(Y)_m$ is 4-chloro, as, for example, in a preferred compound: 4-chloro-(3'-pyridyl)-imino-C-(isobutylthio)methylbenzene.

However, compounds in which $(Y)_m$ represents dihalo substitution are also particularly effective. In such case $(Y)_m$ is preferably dichloro-, and advantageously the chlorine atoms are in the 2,4- or 3,4-positions of the benzene ring.

The compounds of the invention can be prepared by treating a compound of the general formula:

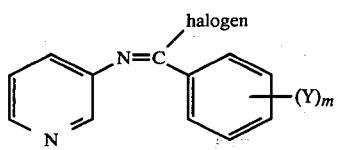

with a compound of the formula

Q—X wherein Q is hydrogen or an alkali metal atom, optionally in the presence of an acid acceptor.

The intermediates of formula II are conveniently prepared by reacting a thionyl halide with the appropriate N-(3'-pyridyl)benzamide of the general formula:

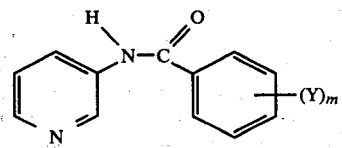

Compounds of Formula I can also be prepared by alkylation of the corresponding thioanilides.

The compounds of formula I have been found to exhibit fungicidal properties.

Accordingly, the invention further provides a fungicidal composition comprising a compound of formula I as defined above in association with at least one inert carrier therefor, and a method of making such a composition which comprises bringing a compound of formula I as defined above into association with at least one inert carrier therefor.

Further in accordance with the invention there is provided a method of protecting a crop fungal attack comprising treating crops subject to or subjected to fungal attack, seeds of such crops or soil in which such crops are growing or are to be grown with a compound of formula I or a composition according to the invention.

A carrier in a composition according to the invention is any material with which the active ingredient is formulated to facilitate application to the locus to be treated, which may, for example, be a plant, seed or soil, or to facilitate storage, transport or handling. A carrier may be a solid or a liquid, including a material which is normally gaseous but which has been compressed to form a liquid, and any of the carriers normally used in formulating fungicidal compositions may be used.

Suitable solid carriers include natural and synthetic clays and silicates, for example, natural silicas such as diatomaceous earths; magnesium silicates, for example, talcs; magnesium aluminum silicates, for example, attapulgites and vermiculities; aluminum silicates, for example, kaolinites, montmorillonites and micas; calcium carbonate; calcium sulfate; synthetic hydrated silicon oxides and synthetic calcium or aluminum silicates; elements, for example, carbon and sulfur; natural and synthetic resins, for example, coumarone resins, polyvinyl chloride, and styrene polymers and copolymers; solid polychlorophenols; bitumen; waxes, for example, beeswax, paraffin wax, and chlorinated mineral waxes; and solid fertilizers, for example, superphosphates.

Suitable liquid carriers include water; alcohols, for example, isopropanol and glycols; ketones, for example, acetone, methyl ethyl ketone, methyl isobutyl ketone and cyclohexanone; ethers; aromatic or araliphatic hydrocarbons, for example, benzene, toluene and xylene; petroleum fractions, for example, kerosine and light mineral oils; chlorinated hydrocarbons, for example, carbon tetrachloride, perchloroethylene and trichloroethane. Mixtures of different liquids are often suitable.

Fungicidal compositions are often formulated and transported in a concentrated form which is subsequently diluted by the user before application. The presence of small amounts of a carrier which is a surface-active agent facilitates this process of dilution. Thus, preferably, at least one carrier in a composition according to the invention is a surface-active agent. For example, a composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example, p-octylphenol or p-octylcresol, with ethylene oxide and/or propylene oxide; sulfates or sulfonates of these condensation products; alkali or alkaline earth salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxide.

The compositions of the invention may, for example, be formulated as wettable powders, dusts, granules, solutions, emulsifiable concentrates, emulsions, suspension concentrates and aerosols. Wettable powders usually contain 25, 50 and 75%w of active ingredient and usually contain, in addition to solid inert carrier, 3–10%w of a dispersing agent and, where necessary, 0–10%w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing 0.5–10%w of active ingredient. Granules are usually prepared to have a size between 10 and 100 BS mesh (1.676–0.152 mm), and may be manufactured by agglomeration or impregnation techniques. Generally, granules will contain 0.5–25%w active ingredient and 0–10%w of additives such as stabilizers, slow-release modifiers and binding agents. Emulsifiable concentrates usually contain, in addition to a solvent and, when necessary, co-solvent, 10–50%w/v active ingredient, 2–20%w/v emulsifiers and 0–20%w/v of other additives such as stabilizers, penetrants and corrosion inhibitors. Suspension concentrates are usually compounded so as to obtain a stable, non-sedimenting flowable product and usually contain 10–75%w active ingredient, 0.5–15%w of dispersing agents, 0.1–10%w of suspending agents such as protective colloids and thixotropic agents, 0–10%w of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick "mayonnaise"-like consistency.

Typical individual compounds of the invention have been prepared as described in the following examples. In each case, the identity of the product was confirmed by appropriate chemical and spectral analyses.

EXAMPLE 1

4-Chloro-(3'-pyridyl)imino-C-(isopropylthio)methylbenzene (1)

A stirred mixture of 7 g of N-(3'-pyridyl)-4-chlorobenzamide and 22.5 ml of thionyl chloride was heated under reflux for two hours. Excess thionyl chloride was evaporated under reduced pressure, and the residue, 4-chloro-(3'-pyridyl)imino-C-(chloro)methylbenzene, was treated with 100 ml of dry pyridine. 4.5 g of isopropyl mercaptan was added and the mixture was stirred and heated at 100°–100° C. for 16 hours. The solvent and other volatile components of the mixture were evaporated under reduced pressure, and the residue was extracted with diethyl ether. The extract was washed with water and dried over anhydrous magnesium sulfate. After evaporation of the ether, the residue was subjected to chromatography on a silica gel column, eluting with diethyl ether/hexane (1:1 v:v), to give 1, as a yellow solid, m.p. 55.5°–57° C.

EXAMPLES 2 TO 15

By similar methods were prepared the compounds listed in Table I.

TABLE I

| Example No. | Compound No. | X | $(Y)_m$ | mp °C. |
|---|---|---|---|---|
| 2 | 2 | —S(CH$_2$)$_3$CH$_3$ | 4-Cl | oil |
| 3 | 3 | —SCH(CH$_3$)CH$_2$CH$_3$ | " | oil |
| 4 | 4 | —SCH$_2$CH$_2$CH$_3$ | " | oil |
| 5 | 5 | —SC(CH$_3$)$_3$ | " | 97 |
| 6 | 6 | —SCH$_2$CH(CH$_3$)$_2$ | " | oil |
| 7 | 7 | —S(CH$_3$)$_3$ | 2,4-Cl$_2$ | 90 |
| 8 | 8 | " | 3,4-Cl$_2$ | 84–86 |
| 9 | 9 | —SCH$_2$CH(CH$_3$)$_2$ | 2,4-Cl$_2$ | oil |
| 10 | 10 | —SC$_3$H$_7$ | 2,4-Cl$_2$ | oil |
| 11 | 11 | —SC(CH$_3$)$_3$ | 4-F | 53 |
| 12 | 12 | —SCH(CH$_3$)$_2$ | 2,4-Cl$_2$ | 43–4 |
| 13 | 13 | —SCH(CH$_3$)CH$_2$CH$_3$ | " | oil |

Fungicidal Activity

To illustrate the fungicidal activity of compounds of the invention, the examples given hereinafter of a wide range of compounds of Formula I and representative of the scope thereof include results obtained by subjecting these compounds to a variety of tests representative of the spectrum of fungus species against which fungicidal compositions are required for use. The following tests were carried out:

(1) Activity against vine downy mildew (*plasmopara viticola*-P.v.-a.)

The test was a direct antisporulant one using a foliar spray. The lower surfaces of leaves of whole vine plants were inoculated by spraying with an aqueous suspension containing 10$^5$ zoosporangia per milliliter 4 days prior to treatment with the test compound. The inoculated plants were kept for 24 hours in a high humidity compartment, 48 hours at glasshouse ambient temperature and humidity and then returned for a further 24 hours to high humidity. The plants then were dried and infected leaves detached and sprayed on the lower surfaces at a dosage of 1 kilogram of active material per hectare using a track sprayer. After drying, the petioles of the sprayed leaves were dipped in water and the leaves returned to high humidity for a further 72 hours incubation, followed by assessment. Assessment was based on the percentage of the leaf area covered by sporulation compared with that on control leaves.

(2) Activity against vine downy mildew (*Plasmopara viticola*-P.v.-t.)

The test was a translaminar protectant one using a foliar spray. The upper surfaces of leaves of whole vine plants were sprayed at a dosage of 1 kilogram of active material per hectare using a track sprayer. The lower surfaces of the leaves were then inoculated, up to 6 hours after treatment with the test compound, by spraying with an aqueous suspension containing $10^5$ zoosporangia per milliliter. The inoculated plants were kept for 24 hours in a high humidity compartment, 4 days at glasshouse ambient temperature and humidity and then returned for a further 24 hours to high humidity. Assessment was based on the percentage of the leaf area covered by sporulation compared with that on control leaves.

(3) Activity against vine grey mold (*Botrytis cinerea*-B.c.)

The test was a direct eradicant one using a foliar spray. The under-surfaces of detached vine leaves were inoculated by pipetting 10 large drops of an aqueous suspension containing $5 \times 10^5$ conidia per milliliter onto them. The inoculated leaves were kept uncovered overnight during which time the drops containing the conidia slowly dried. By this time the fungus had penetrated the leaf and a visible necrotic lesion sometimes was apparent where the drop was made. The infected regions were sprayed directly with a dosage of one kilogram of active material per hectare using a track sprayer. When the spray had dried the leaves were covered with petri dish lids and the disease allowed to develop under the moist conditions. The extent of the necrotic lesion beyond the original drop together with the degree of sporulation was compared with that on control leaves.

(4) Activity against potato late blight (*Phytophthora infestans*-P.i.-e.)

The test was a direct eradicant one using a foliar spray. The upper surfaces of the leaves of potato plants (12-18 centimeters high, in monopots) were inoculated by spraying with an aqueous suspension containing $5 \times 10^3$ zoosporangia per milliliter 16-19 hours prior to treatment with the test compound. The inoculated plants were kept overnight at high humidity and then allowed to dry before spraying at a dosage of 1 kilogram of active material per hectare using a track sprayer. After spraying, the plants were returned to high humidity for a further period of 48 hours. Assessment was based on a comparison between the levels of disease on the treated and control plants.

(5) Activity against potato late blight (*Phytophthora infestans*-P.i.-p.)

The test measured the direct protectant activity of compounds applied as a foliar spray. Tomato plants, cultivar Ailsa Craig, 1-15 cms high, in monopots were used. The whole plant was sprayed at a dosage of 1 kilogram of active material per hectare using a track sprayer. The plant then was inoculated up to 6 hours after treatment with the test compound, by spraying with an aqueous suspension containing $5 \times 10^3$ zoosporangia per milliliter. The inoculated plants were kept in high humidity for 3 days. Assessment was based on a comparison between the levels of disease on the treated and control plants.

(6) Activity against barley powdery mildew (*Erysiphe graminis*-E.g.)

The test measured the direct antisporulant activity of compounds applied as a foliar spray. For each compound about 40 barley seedlings were grown to the one-leaf stage in a plastic pot of sterile potting compost. Inoculation was effected by dusting the leaves with conidia of *Erysiphe graminis* spp. *hordei*. Twenty-four hours after inoculation the seedlings were sprayed with a solution of the compound in a mixture of acetone (50%), surfactant (0.049%) and water using a track sprayer. The rate of application was equivalent to 1 kilogram of active material per hectare. First assessment of disease was made 5 days after treatment, when the overall level of sporulation on the treated pots was compared with that on control pots.

(7) Acitivity against wheat brown rust (*Puccinia recondita*-P.r.)

The test was a direct antisporulant one using a foliar spray. Pots containing about 25 wheat seedlings per pot, at first leaf stage, were inoculated by spraying the leaves with an aqueous suspension, containing $10^5$ spores per milliliters plus a little Triton X-155, 20-24 hours before treatment with the compound under test. The inoculated plants were kept overnight in a high humidity compartment, dried at glasshouse ambient temperature and then sprayed at a dosage of 1 kilogram of active material per hectare using a track sprayer. After treatment, the plants were kept at glasshouse ambient temperature and assessment made about 11 days after treatment. Assessment was based on the relative density of sporulating pustules per plant compared with that on control plants.

(8) Activity against broad bean rust (*Uromyces fabae*-U.f.)

The test was a translaminar antisporulant one using foliar spray. Pots containing one plant per pot were inoculated by spraying an aqueous suspension, containing $5 \times 10^4$ spores per milliliter plus a little Triton X-155, onto the undersurface of each leaf 20-24 hours before treatment with test compound. The inoculated plants were kept overnight in a high humidity compartment, dried at glasshouse ambient temperature and then sprayed on the leaf upper surface, at a dosage of one kilogram per hectare of active material using a track sprayer. After treatment the plants were kept at glasshouse temperature and assessment made 11-14 days after treatment. Symptoms were assessed on the relative density of sporulating pustules per plant compared with that on control plants.

(9) Activity against rice leaf blast (*Pyricularia oryzae*-P.o.)

The test was a direct eradicant one using a foliar spray. The leaves of rice seedlings (about 30 seedlings per pot) were sprayed with an aqueous suspension containing $10^5$ spores per milliliter 20-24 hours prior to treatment with the test compound. The inoculated plants were kept overnight in high humidity and then allowed to dry before spraying at a dosage of 1 kilogram of active material per hectare using a track sprayer. After treatment, the plants were kept in a rice compartment at 25°–30° C. and high humidity. Assessments were made 4–5 days after treatment and were based on the density of necrotic lesions and the degree of withering when compared with control plants.

(10) Activity against rice sheath blight (*Pellicularia sasakii*-P.s.)

The test was a direct eradicant one using foliar spray. 20–24 hours prior to treatment with the test compound, rice seedlings (about 30 seedlings per pot) were sprayed with 5 milliters of an aqueous suspension containing 0.2 gram of crushed sclerotia/mycelium per milliliter. The inoculated plants were kept overnight in a humid cabinet maintained at 25°–30° C., followed by spraying at a dosage of 1 kilogram of active material per hectare. The treated plants then were returned to high humidity for a further period of 3–4 days. With this disease brown lesions were seen that started at the base of the sheath and extended upwards. Assessments were made on the number and extent of the lesions when compared with the controls.

(11) Activity against apple powdery mildew (*Podospmaera leucotricha*-P.l.)

The test was a direct anti-sporulant one using a foliar spray. The upper surfaces of leaves of whole apple seedlings were inoculated by spraying with an aqueous suspension containing $10^5$ conidia per milliliter 2 days prior to treatment with the test compound. The inoculated plants were immediately dried and kept at glasshouse ambient temperatures and humidity prior to treatment. The plants were sprayed at a dosage of 1 kilogram of active material per hectare using a track sprayer. After drying the plants were returned to a compartment at ambient temperature and humidity for up to 9 days, followed by assessment. Assessment was based on the percentage of the leaf area covered by sporulation compared with that on leaves of control plants.

(12) Activity against peanut leaf spot (*Cercopsora arachidicola*-C.a.)

The test was a direct eradicant one using a foliar spray. The upper surfaces of the leaves of peanut plants (12–20 centimeters high, in monopots) were inoculated by spraying with an aqueous suspension containing $10^5$ conidia per milliter 40–43 hours prior to treatment with the test compound. The inoculated plants were kept at high humidity and then allowed to dry during the interval between inoculation and treatment by spraying at a dosage of 1 kilogram of active material per hectare using a track sprayer. After spraying, the plants were moved to a humid compartment at 25°–28° C. for a further period of up to 10 days. Assessment was based on a comparison between the levels of disease on the treated and control plants.

In these tests, compounds 2 through 14 were not tested with respect to the organisms: P.o. and P.s., compounds 1–14 were not tested with respect to the organisms: P.l. and C.a., and compounds 15–36 were not tested with respect to the organism: P.s.

The extent of disease control was expressed as a control rating according to the criteria:
0=less than 50% disease control
1=50–80% disease control
2=greater than 80% disease control The disease control ratings are given in Table II for the compounds described in the previous Examples.

TABLE II

| Organism | Compounds having the Rating* | |
|---|---|---|
| | 2 | 1 |
| P.v.-a. | | |
| P.v.-t. | 1,9 | 22,23 |
| B.c. | 7,13 | |
| P.i.-e. | | |
| P.i.-p. | 10 | 4 |
| E.g. | 1,2,3,4,5,6, 7,9,10,12 | |
| P.r. | 7 | 5 (systemic), 21,22 |
| U.f. | 7,9 | |
| P.o. | | 1 |
| P.s. | 1 | |
| P.l. | 7,8,9,10,11 | |
| C.a. | 7,9,10 | 8 |

*Otherwise the test compounds had a "0" rating with respect to the organisms.

We claim:
1. A compound of the formula

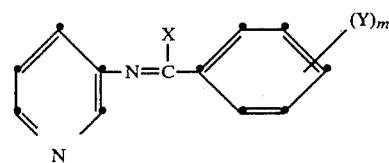

wherein X is alkylthio of from one to six carbon atoms; m is 1 or 2; and Y is halogen, and acid-addition salts thereof.

2. A compound according to claim 1 wherein Y is chlorine.

3. A compound according to claim 2 wherein m is one and the chlorine atom is bonded to the carbon atom in the para-position of the ring.

4. A fungicidal composition comprising a fungicidally effective amount of a compound of claim 1 in association with at least one inert carrier thereof.

5. A method of protecting a crop from fungal attack comprising treating crops subject to or subjected to fungal attack, seeds of such crops or soil in which such crops are growing or are to be grown with a fungicidally effective amount of a compound according to claim 1, or a composition according to claim 4.

6. A fungicidal composition comprising a fungicidally effective amount of a compound of claim 2 in association with at least one inert carrier therefor.

7. A method of protecting a crop from fungal attack comprising treating crops subject to or subjected to fungal attack, seeds of such crops or soil in which such crops are growing or are to be grown with a fungicidally effective amount of a compound according to claim 2.

* * * * *